United States Patent [19]

Sadowsky

[11] Patent Number: 5,042,094
[45] Date of Patent: Aug. 27, 1991

[54] EYE WEAR WITH PROSTHETIC PARTS FOR SMALL CHILDREN

[76] Inventor: Cynthia L. Sadowsky, 2601 W. Calle Genova, Tucson, Ariz. 85745

[21] Appl. No.: 539,205

[22] Filed: Jun. 18, 1990

[51] Int. Cl.⁵ .......................... A61F 9/02; G02C 3/00
[52] U.S. Cl. ............................................. 2/439; 2/9; 2/426; 2/445; 2/448; 2/454; 351/156
[58] Field of Search ...................... 2/9, 426, 439, 440, 2/442, 445, 446, 448, 454; 351/156, 157, 122, 139, 124, 41

[56] References Cited

U.S. PATENT DOCUMENTS

| D. 178,328 | 7/1956 | Tilton | D57/1 |
|---|---|---|---|
| 1,754,694 | 4/1930 | Neuwirth | 2/440 |
| 1,819,738 | 8/1931 | Daniels | 351/156 |
| 3,173,147 | 3/1965 | Gross et al. | 351/156 |
| 3,378,851 | 4/1968 | McBrayer | 2/454 |
| 4,520,510 | 6/1985 | Daigle | 2/426 |
| 4,930,885 | 6/1990 | Laschober | 351/156 |
| 4,953,967 | 9/1990 | Somerville | 351/156 |

FOREIGN PATENT DOCUMENTS

| 2106962 | 8/1972 | Fed. Rep. of Germany | 351/41 |
|---|---|---|---|
| 2410586 | 9/1975 | Fed. Rep. of Germany | 351/156 |
| 378972 | 10/1907 | France | 2/439 |
| 1535556 | 7/1968 | France | 351/122 |
| 320163 | 8/1934 | Italy | 351/41 |

Primary Examiner—Peter Nerbun
Assistant Examiner—Michael A. Neas
Attorney, Agent, or Firm—Antonio R. Durando; Harry M. Weiss

[57] ABSTRACT

Practical, safe and comfortable eye wear for babies and small children. A rigid shatterproof lens portion encased in a padded and pliable frame that is strapped around the baby's head. Specially designed nose and temple pieces are incorporated into the frame to provide support for the frame on the baby's face in the absence of the normally supportive bone structure of adults.

9 Claims, 1 Drawing Sheet

EYE WEAR WITH PROSTHETIC PARTS FOR SMALL CHILDREN

BACKGROUND OF THE INVENTION

1. Field of the Invention

This invention pertains to the general field of eye glasses and protective sun shades. In particular, it provides a new and improved type of sunglasses for babies and little children whose undeveloped facial features do not allow them to wear regularly shaped eye wear.

2. Description of the Prior Art

People have used different kinds of eye wear for centuries, either for protective, prosthetic or aesthetic purposes. Typically, eyeglasses and similar articles consist of a transparent portion encased in a frame that fits around the wearer's eyes. The transparent portion may be optically inert or include corrective lenses to improve vision; it may also be darkened and coated with a radiation filtering film for comfort and protection from sunlight. Shatterproof material is often used for safety in glasses or goggles to be worn in dangerous environments.

Similarly, frames vary widely in shape and material according to the different objectives for which they have been designed.

Safety goggles may be shaped to enclose the eyes completely and equipped with a strap to hold them securely in place. A retaining strap is especially useful for athletic applications. On the other hand, fashion considerations have produced a very wide variety of stylized shapes in sunglasses that offer no particular protection but meet the esthetic expectations of the public.

The frame of regular eyeglasses normally includes a bow, which holds the lenses in place, a bridge, which rests on the nose of the wearer for support, and two temples jointed to the bow and passing over the ear on each side of the head. This type of frame is impractical for use on babies and little children because their facial features are not sufficiently developed to allow them to wear normal eyeglasses. Their noses and ears are too small to support the bridge and temples of the frame; as a result, the glasses tend to create discomfort and fall off at the slightest movement of the child.

Therefore, there still remains a need for eye wear that is suitable for babies and little children. In particular, a need exists for practical and safe baby sun shades and prescription glasses.

BRIEF SUMMARY OF THE INVENTION

This invention consists of a new method and apparatus for providing practical, safe and comfortable eye wear for babies and small children. One objective of the invention is the development of a frame that fits the typical facial features of a baby, so that it can be worn without the necessity of any particular adaptation involving extraneous accessories to hold the glasses in place.

Another objective is the modification of the shape of the frame in order to provide comfortable wear on the face of the baby. This purpose is particularly important because babies are not able themselves to make adjustments that would alleviate discomfort.

Yet another goal of the invention is that the eye wear be safe and afford the protection for which it is worn. Whether for shading from sun light or for vision correction, the article must be child-proof in every respect.

Finally, a further objective of this invention is the realization of the above mentioned goals in an economical and commercially viable manner. This is done by utilizing simple components that are either already available in the open market or can be produced at competitive prices.

Therefore, the baby eye wear of this invention consists of a rigid shatter-proof lens portion encased in, or incorporated with, a padded and adjustable fabric frame that is strapped around the baby's head. Specially designed nose and temple pieces are incorporated into the frame to provide support for the frame on the baby's face in the absence of the normally supportive bone structure of adults.

Various other purposes and advantages of the invention will become clear from its description in the specifications that follow and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DETAILED DESCRIPTION OF THE INVENTION

The substance of this invention lies in the idea that the cranial and facial features of babies and small children are not fully developed; therefore, the bone structure of the nose and temples and the shape and size of the ears, which all are instrumental to the proper use of eye wear, are not sufficiently developed and pronounced for normal frame designs.

The upper part of baby noses tend to be flat and unsuitable for fitting snugly into the bridge of standard frames; thus, they provide little support for the glasses, which in turn tend to free float on the baby's face. Similarly, a baby's ears are normally not pronounced enough to provide support for the frame's temples. Without a rigid anchor around the nose and over the ears, the eye wear frame is free to move loosely and sit obliquely on the baby's forehead. The result is that such eye wear becomes functionally inefficient and possibly unsafe because of the potential for injury caused by its erratic position on the baby's face.

The eye wear of this invention aims at correcting these deficiencies by addressing each specific concern mentioned above. Therefore, eye wear according to this invention features prosthetic members in the nose and temple portions of the frame to supply the missing supporting structure. Moreover, the frame is either constructed or covered with soft, pliable and resilient material for further adaptation to the contour of the baby's face. Instead of temples to fit over the ears, the frame is held in place by a padded strap around the back of the baby's head.

Figure 1:
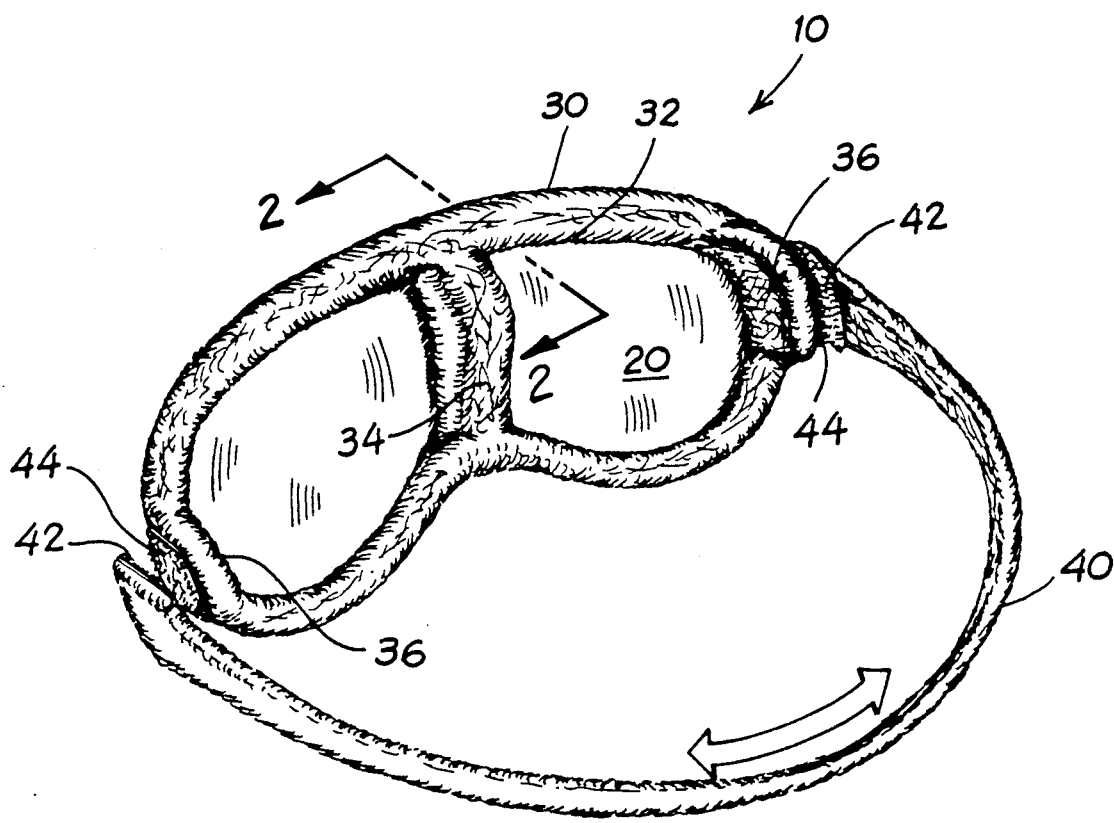
FIG. 1 illustrates a perspective view of the preferred embodiment of baby eye wear according to this invention.
Figure 2:
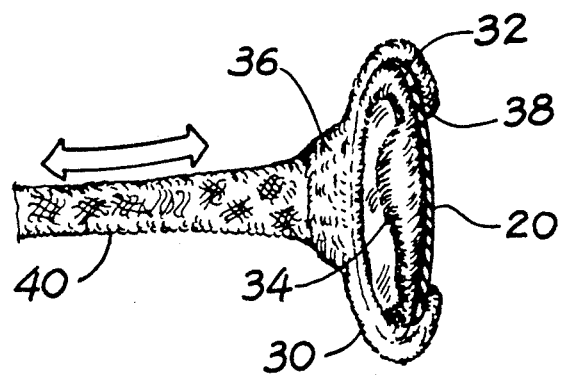
FIG. 2 shows a cross-sectional view of the eye wear shown in of FIG. 1 taken from line 2—2.

Referring to FIGS. 1 and 2, a particular embodiment of this invention is shown. Like parts in the various figures of the drawings are identified with the same reference symbols. While only one of many ways to effect the same result, the apparatus in these figures is believed to be the best example for practicing the invention in an economical and operationally efficient way.

FIG. 1 illustrates an example of eye wear according to this invention. Viewed from the back, it shows baby shades 10 that generally include a lens 20, a frame 30, and a strap 40. The lens 10 may be comprised of a single sheet, as in FIG. 1, or of multiple lenses, as in standard eyeglasses (not shown); it may be flat or slightly concave toward the inside, and completely clear or tinted for radiation protection. Finally, the lens may be fabricated with any suitable material known in the art, with the additional requirement that it be completely safe for children use.

The frame 30 consists of a rim 32, shaped like the perimeter of the lens 20, and of prosthetic appendages 34 and 36. The frame is constructed with resilient material, preferably also soft and pliable, so that it can stretch to receive and contract to hold in place the lens 20 in an inner groove 38, shown in FIG. 2. While any plastic material is acceptable, the purposes of the invention are better served by the use of spongy material covered by soft fabric, such as terry cloth, because of the yielding characteristics and the softer interaction of the combination with delicate baby skin.

A nose piece 34 is attached to the upper and lower portions of the rim 32 to form a vertical prosthetic member to fill the space between the interior midportion of the lens and the nasal surface on the face of the baby. The nose piece is shaped with a convex curvature to fit the typical indentation between a baby's forehead and nose tip. Although not necessarily attached to the lens 20, the nose piece 34 also functions as structural reinforcement to keep the upper and lower portions of the rim 32 tied and hold the lens in place in the groove 38.

Temple pieces 36 are either formed into or attached to the lateral ends of the rim 32 for similar prosthetic purposes. Each temple piece 36 is shaped with a convex curvature to fill the space between the forehead and the cheek bone (zygomatic bone) on the side of each eye. Though not essential to the invention, these prosthetic temple pieces are particularly important when the lens 20 is flat because of the corresponding greater need for structural support as the frame is kept pressed against the baby's temples.

Although not described in the figures, the lense and frame portions of this invention can also be produced in a single piece, especially when plastic material is adopted. It is anticipated that this uni-body construction would reduce manufacturing costs significantly.

Finally, a strap 40 must be provided in order to comfortably hold the eye wear in place. This strap may consist of a removable band attached to the outer lateral portions of the frame by means of fiber loop fastening components 44, well known under the mark "Velcro," cooperatively placed on its ends 42 and on the frame, so that the band can be affixed and adjusted to comfortably fit around the baby's head. The strap 40 may also be slightly elasticized, to improve its fastening characteristics, and padded, to insure a more comfortable wear.

Therefore, while the present invention has been shown and described herein in what is believed to be the most practical and preferred embodiment, it is recognized that departures can be made therefrom within the scope of the invention, which is not to be limited to the details disclosed herein but is to be accorded the full scope of the claims so as to embrace any and all equivalent apparatuses and methods.

I claim:

1. An eye wear apparatus for babies and small children, comprising:
   (a) a transparent lens portion;
   (b) a frame encasing said transparent lens portion and having prosthetic parts to achieve a contour fit on the face of a wearer; and
   (c) means for securely and safely retaining said frame in place;
   wherein said prosthetic parts comprise a nose piece shaped like the upper portion of an adult nose and attached vertically to an interior mid-section of said frame for contact with the wearer's face in the area between the forehead and the nose, and wherein said prosthetic parts further comprise two temple pieces shaped like the arch between the forehead and the zygomatic bone on each side of the wearer's face, each of said temple pieces being attached vertically to an interior portion of each lateral end of said frame for contact with the wearer's face and structural support of the frame while under tension from said means for securely and safely retaining said frame in place.

2. The apparatus described in claim 7, wherein said frame consists of a structure made of soft, pliable and resilient material generally shaped in its unstretched condition like the outer perimeter of said transparent lens portion, having an inner fold forming a groove for receiving and holding in place in its stretched condition said transparent lens portion.

3. The apparatus described in claim 1, wherein said frame and said lens portion consist of a single structure made of plastic material, and wherein said frame is covered with padding material.

4. The apparatus described in claim 2, wherein said means for securely and safely retaining said frame in place consists of an adjustable elastic strap attached to the right and left ends of said frame, so that it may be worn around the wearer's head.

5. The apparatus described in claim 2, wherein said means for securely and safely retaining said frame in place consists of a removable band attached to said frame by means of fiber loop fastening components cooperatively placed on its ends and on the right and left ends of the frame, so that said removable band can be affixed to the frame and it may be adjusted to comfortably fit around the wearer'head.

6. The apparatus described in claim 5, wherein said transparent lens portion is shatterproof.

7. The apparatus described in claim 6, wherein said adjustable elastic strap is padded.

8. An eye wear apparatus for babies and small children, comprising:
   (a) a shatterproof, tinted, and transparent lens portion for vision and protection against radiation and shock;
   (b) a frame to encase said lens portion consisting of a structure made of soft, pliable and resilient material generally shaped in its unstretched condition like the outer perimeter of said lens portion, having an inner fold forming a groove for receiving and holding in place in its stretched condition said lens portion;

(c) a prosthetic nose piece shaped like the upper portion of an adult nose and attached vertically to an interior mid-section of said frame for contact with a wearer's face in the area between the forehead and the nose;

(d) two prosthetic temple pieces shaped like the arch between the forehead and the zygomatic bone on each side of the wearer's face, each of said temple pieces being attached vertically to an interior portion of each lateral end of said frame for contact with, and for structural support of, the frame against the wearer's face; and (e) a padded, removable band attached to said frame by means of fiber loop fastening components cooperatively placed on its ends and on the right and left ends of the frame, so that said removable band can be affixed to the frame and it may be adjusted to comfortably fit around the wearer's head.

9. The apparatus described in claim 8, wherein said frame consists of an inner core covered with terry cloth.

* * * * *